(12) United States Patent
Cheng

(10) Patent No.: US 11,324,927 B2
(45) Date of Patent: May 10, 2022

(54) CATHETER ASSEMBLY HAVING AN INJECTION PORT AND RELATED METHODS

(71) Applicant: Becton, Dickinson and Company, Franklin Lakes, NJ (US)

(72) Inventor: Kiat Jin Cheng, Bishan (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 175 days.

(21) Appl. No.: 16/878,359

(22) Filed: May 19, 2020

(65) Prior Publication Data

US 2020/0376234 A1   Dec. 3, 2020

Related U.S. Application Data

(60) Provisional application No. 62/854,123, filed on May 29, 2019.

(51) Int. Cl.
| | |
|---|---|
| *A61M 25/06* | (2006.01) |
| *A61M 25/00* | (2006.01) |
| *A61M 39/10* | (2006.01) |
| *A61M 39/22* | (2006.01) |
| *A61M 25/01* | (2006.01) |

(52) U.S. Cl.
CPC .... *A61M 25/0606* (2013.01); *A61M 25/0015* (2013.01); *A61M 39/10* (2013.01); *A61M 39/22* (2013.01); *A61M 2025/018* (2013.01); *A61M 2039/1077* (2013.01)

(58) Field of Classification Search
CPC .......... A61M 25/0606; A61M 25/0015; A61M 39/10; A61M 39/22; A61M 2025/018

USPC .......................................................... 604/523
See application file for complete search history.

(56) References Cited

U.S. PATENT DOCUMENTS

| | | | |
|---|---|---|---|
| 2015/0202421 A1 | 7/2015 | Ma et al. | |
| 2015/0202422 A1* | 7/2015 | Ma ................... | A61M 25/0606 |
| | | | 604/167.02 |
| 2017/0281922 A1* | 10/2017 | Baid ................... | A61M 39/22 |
| 2019/0091462 A1* | 3/2019 | Bihlmaier ............ | A61M 39/16 |

FOREIGN PATENT DOCUMENTS

| | | |
|---|---|---|
| WO | 2016/036468 | 3/2016 |
| WO | 2016/142410 | 9/2016 |

\* cited by examiner

*Primary Examiner* — Phillip A Gray
(74) *Attorney, Agent, or Firm* — Kirton McConkie; Whitney Blair; Kevin Stinger

(57) ABSTRACT

A catheter assembly may include a catheter adapter. A body of the catheter adapter may include a distal end, a proximal end, and a first lumen extending through the distal end and the proximal end. The catheter adapter may include a side port, which may extend outwardly from the body. The side port may include a second lumen, which may be perpendicular to the first lumen. The catheter assembly may include a catheter extending distally from the distal end of the body. The catheter assembly may include a valve disposed within the first lumen. The valve may include an outer surface that is cylindrical and may seal the first lumen from the second lumen. The catheter assembly may include a divider disposed with the second lumen. The divider may divide the second lumen into a plurality of openings and may increase a burst value of the valve.

20 Claims, 9 Drawing Sheets

CATHETER ASSEMBLY HAVING AN INJECTION PORT AND RELATED METHODS

RELATED APPLICATIONS

This application claims the benefit of U.S. Provisional Patent Application No. 62/854,123, filed May 29, 2020, and entitled CATHETER ASSEMBLY HAVING AN INJECTION PORT AND RELATED METHODS, which is incorporated herein in its entirety.

BACKGROUND

Catheters are generally used for parenteral nutrition, intravenous fluid replacement, and administering analgesics and antibiotics. Catheters are also used for blood draw. Catheters can be inserted at the bedside using sterile techniques and can remain in place for several weeks.

A common type catheter is an over-the-needle catheter. As its name implies, a catheter that is "over-the-needle" may be mounted over an introducer needle having a sharp distal tip. The sharp distal tip may be used to pierce skin and a vein of a patient. Insertion of the catheter into the vein may follow the piercing of the vein by the introducer needle. The introducer needle typically has the sharp distal tip to pierce skin and the vein of the patient with minimal resistance to minimize the pain to the patient.

The introducer needle is generally placed at a steep inclined angle with respect to a surface of the skin and a longitudinal dimension of the vein to be pierced to allow penetration through the skin and a wall of the vein. The needle and the catheter are generally inserted with a bevel of the introducer needle facing away from the skin of the patient. After the tip of the introducer needle pierces the wall, the angle of the insertion is lowered to be able to slide the introducer needle and the catheter into the vein a distance sufficient to properly position the catheter in the vein. Once placement of the introducer needle within the vein has been confirmed, the user may temporarily occlude flow in the vein and withdraw the introducer needle, leaving the catheter in place for future fluid infusion and/or blood withdrawal.

The subject matter claimed herein is not limited to embodiments that solve any disadvantages or that operate only in environments such as those described above. Rather, this background is only provided to illustrate one example technology area where some implementations described herein may be practiced.

SUMMARY OF THE INVENTION

The present disclosure relates generally to a catheter assembly that may be used for power injection, as well as related devices, systems, and methods. "Power injection" may refer to infusion of large amounts of fluid in a short period of time. In some embodiments, a catheter assembly of the present disclosure may facilitate high flow rates and maintenance of a high pressure within a catheter adapter of the catheter assembly while also maintaining an integrity of a valve disposed within the catheter adapter. In some embodiments, the catheter assembly may increase a breaking threshold (i.e. burst value) of the valve, allowing fluid to be infused into the catheter adapter at high pressures.

In some embodiments, the catheter adapter may include a body, which may include a distal end, a proximal end, and a first lumen extending through the distal end and the proximal end. In some embodiments, a side port of the catheter adapter may extend outwardly from the body and may be disposed between the distal end and the proximal end. In some embodiments, the side port may include a second lumen perpendicular to the first lumen.

In some embodiments, the catheter assembly may include a catheter, which may extend distally from the distal end of the body. In some embodiments, the catheter assembly may include a valve disposed within the first lumen. In some embodiments, the valve may seal the first lumen from the second lumen. In some embodiments, an outer surface of the valve may be cylindrical.

In some embodiments, the catheter assembly may include a divider, which may be disposed with the second lumen. In some embodiments, the catheter adapter and the divider may be monolithically formed as a single unit. In some embodiments, the divider may divide the second lumen into multiple openings. In some embodiments, the divider may be proximate the first lumen. In some embodiments, the divider may contact the valve. In some embodiments, the divider may be symmetrical. In some embodiments, one or more of the multiple openings may be identical. In some embodiments, the divider may include various shapes and patterns.

In some embodiments, the catheter adapter may include an inner surface, which may form the second lumen. In some embodiments, outer edges of the plurality of openings may form or be aligned with a shape, which may be symmetrical. In some embodiments, the divider may be linear and may extend from one side of the shape to another side of the shape. In some embodiments, the divider may be perpendicular to a longitudinal axis of the catheter adapter. In some embodiments, the divider may be parallel to the longitudinal axis of the catheter adapter.

In some embodiments, the divider may include multiple arms, which may extend from the shape to a central axis of the second lumen. In some embodiments, the divider may include X-shape. In these embodiments, the multiple arms may include a first arm, a second arm, a third arm, and a fourth arm. In some embodiments, two of the first arm, the second arm, the third arm, and the fourth arm may be parallel to the longitudinal axis of the catheter adapter. In some embodiments, the first arm, the second arm, the third arm, and the fourth arm may be offset from the longitudinal axis of the catheter adapter.

In some embodiments, the divider may include a Y-shape. In these embodiments, the multiple arms may include the first arm, the second arm, and the third arm. In some embodiments, one of the first arm, the second arm, and the third arm may be parallel to the longitudinal axis of the catheter adapter and may point distally. In some embodiments, one of the first arm, the second arm, and the third arm may be parallel to the longitudinal axis of the catheter adapter and may point proximally.

In some embodiments, a method of delivering fluid into the catheter adapter may include coupling a power injection device to the side port of the catheter adapter. In some embodiments, the method may include delivering fluid, via the power injection device, into the side port at a pressure. In some embodiments, an integrity of the valve may be maintained in response to delivering the fluid into the side port at the pressure. In some embodiments, the pressure may not exceed a burst value of the valve.

In some embodiments, the pressure may be greater than 348 psi. In some embodiments, the pressure may be between 348 psi and 478 psi. In some embodiments, the pressure may be between 348 psi and 728 psi. In some embodiments, the pressure may be between 300 psi and 800 psi. In some embodiments, the pressure may be between 350 psi and 800 psi. In some embodiments, the pressure may be between 700 psi and 1000 psi. In some embodiments, the pressure may be between 300 psi and 400 psi, between 400 psi and 500 psi, between 500 psi and 600 psi, between 600 psi and 700 psi, between 700 psi and 800 psi, or between 800 psi and 900 psi. In some embodiments, in response to delivering the fluid into the side port at the pressure, the divider may inhibit expansion of the valve and/or shifting of the valve in a proximal direction and a distal direction.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Figure 1A:
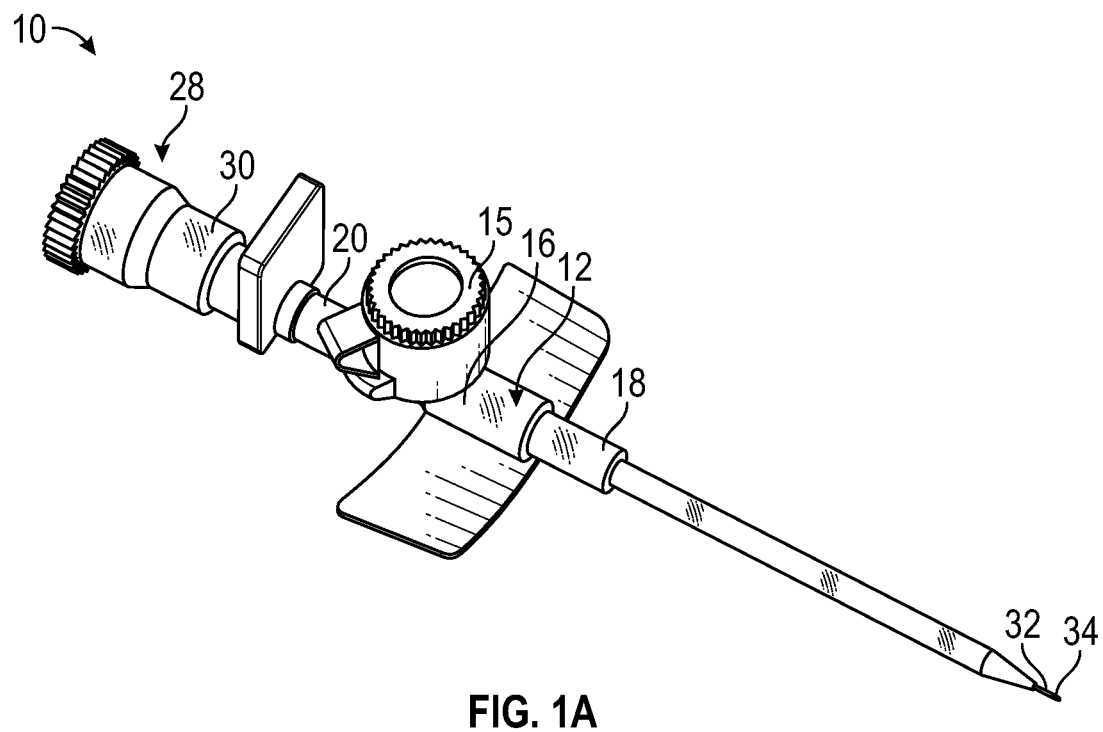
FIG. 1A is an upper perspective view of a prior art catheter assembly.
Figure 1B:
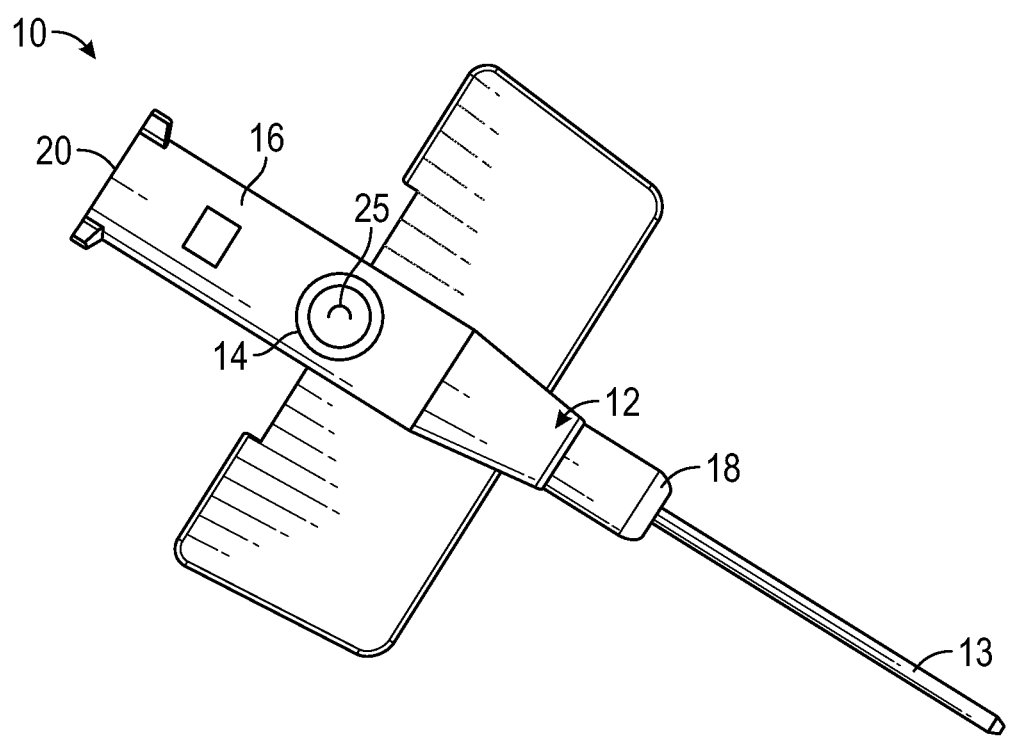
FIG. 1B is a top view of the prior art catheter assembly, illustrating an example cap removed.

Referring now to FIGS. 1A-1B, a prior art catheter assembly 10 is illustrated. The prior art catheter assembly 10 may correspond to the BD VENFLON™ Pro Safety Shielded IV Catheter or another catheter assembly. The prior art catheter assembly 10 includes a catheter adapter 12 and a catheter 13 extending distally from the catheter adapter 12. The catheter adapter 12 includes a body 16, which includes a distal end 18, a proximal end 20, and a lumen 22 extending through the distal end 18 and the proximal end 20. The catheter adapter 12 includes a side port 14 extending outwardly from the body 16 and may be covered by a removable cap 15. A valve 24 is disposed in the lumen 22 and seals the side port 14 from the lumen 22.

The prior art catheter assembly 10 may be unable to withstand the pressure that is delivered by a power injection device 26 coupled to the side port 14, which may be used for power injection. The minimum pressure required for power injection, according to ISO 10555-1, is 300 psi. However, it has been shown that even pressures below 300 psi may exceed the burst value of the valve 24 in the prior art catheter assembly 10, resulting in a rupture or break 25 of the valve 24, as illustrated, for example, in FIG. 1B. The valve 24 may be the weakest component of the prior art catheter assembly 10.

Figure 1C:
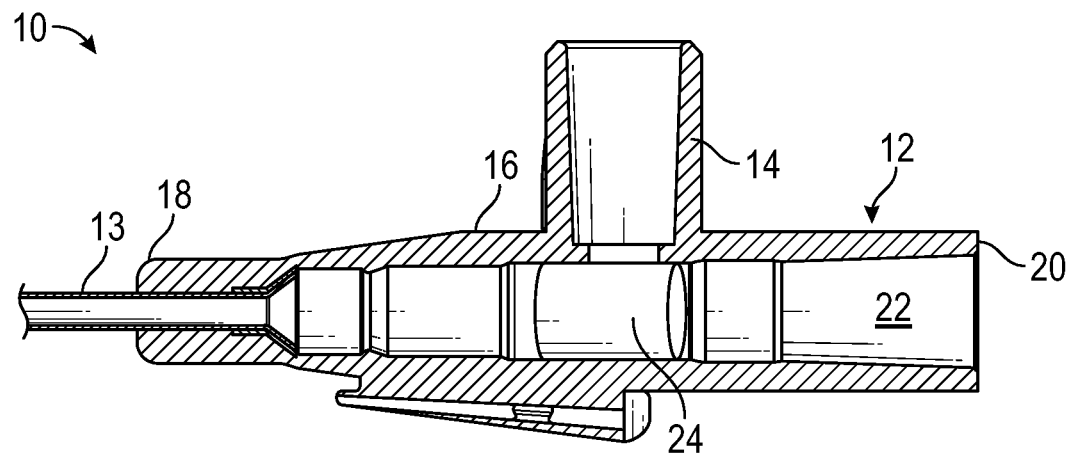
FIG. 1C is a cross-sectional view of the prior art catheter assembly.
Figure 1D:
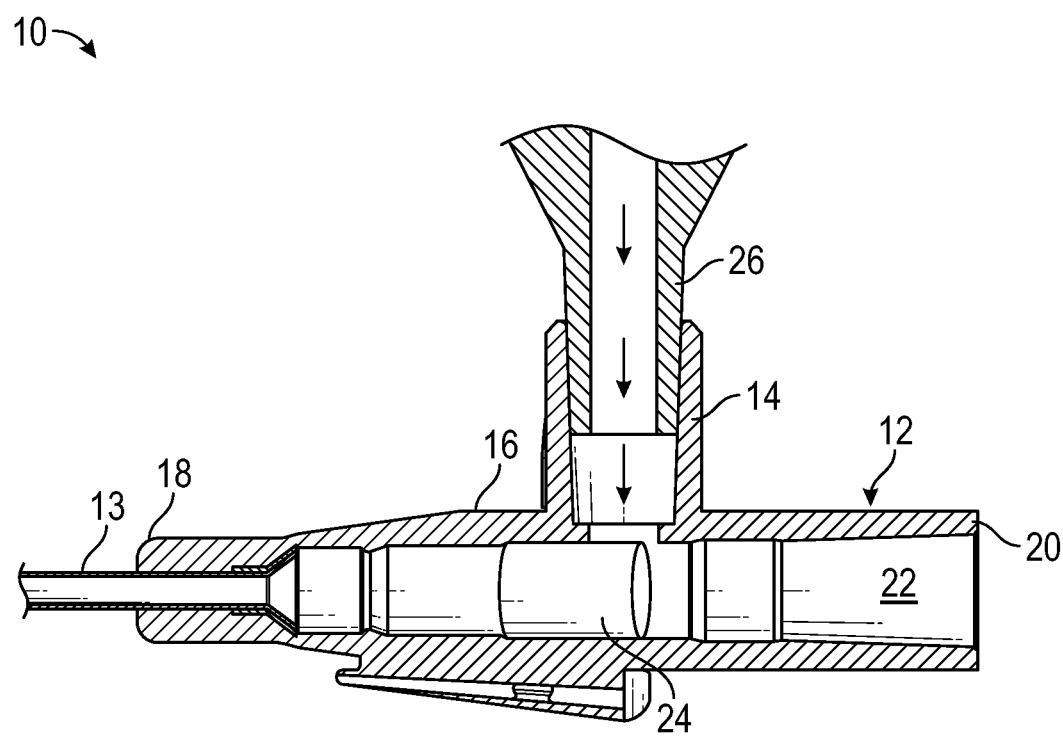
FIG. 1D is a cross-sectional view of the prior art catheter assembly, illustrating an example power injection device delivering fluid into the catheter assembly.

Further, the valve 24 may shift in a distal direction or a proximal direction in response to power injection. Referring now to FIGS. 1C-1D, in response to the power injection device 26 delivering the fluid at a high pressure, such as above 300 psi, the fluid may flow between an inner surface of the catheter adapter 12 and an outer surface of the valve 24 in a manner that shifts the valve 24 from its original position, illustrated in FIG. 1C, to a distal position, illustrated in FIG. 1D, or a proximal position. Thus, the valve 24 may be prevented from resealing the side port 14 from the lumen 22 after completion of the power injection and may no longer be functional.

In some embodiments, the prior art catheter assembly 10 may be removably coupled to a prior art needle assembly 28, which may include a needle hub 30 and an introducer needle 32. In some embodiments, the introducer needle 32 may include a sharp distal tip 34. In some embodiments, a proximal end of the introducer needle 32 may be secured within the needle hub 30. In some embodiments, the introducer needle 32 may extend through the catheter 13 when the prior art catheter assembly 10 is in an insertion position ready for insertion into vasculature of a patient, as illustrated, for example, in FIG. 1A.

In some embodiments, in response to the introducer needle 32 being inserted into the vasculature of the patient, flashback of blood may flow through the sharp distal tip 34 of the introducer needle 32 and may be visible to a clinician between the introducer needle 32 and the catheter 13 and/or at another location within the prior art catheter assembly 10.

In some embodiments, in response to confirmation via the blood flashback that the catheter 13 is positioned within vasculature of the patient, the prior art needle assembly 28 may be removed from the prior art catheter assembly 10, as illustrated in FIG. 1B. In some embodiments, when the prior art needle assembly 28 is coupled to the prior art catheter assembly 10, as illustrated, for example, in FIG. 1A, the introducer needle 32 of the prior art needle assembly 28 may extend through the valve 24 disposed within the lumen 22 of the catheter adapter 12.

Figure 2:
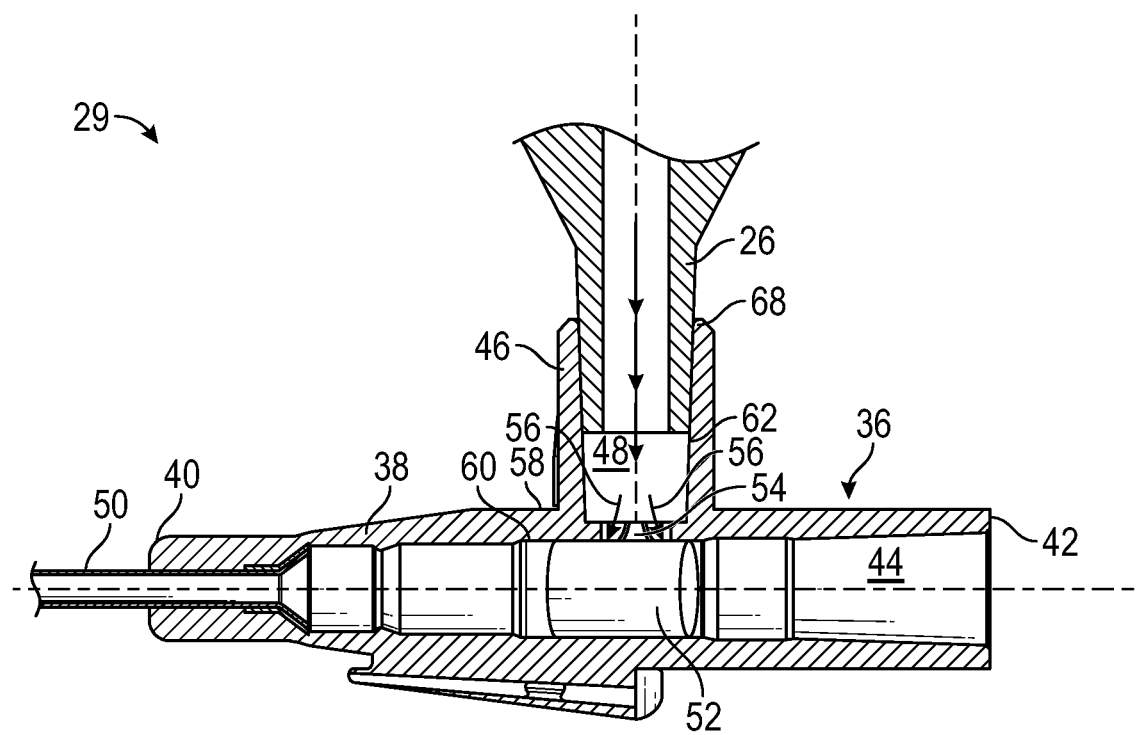
FIG. 2 is a cross-sectional view of another catheter assembly, according to some embodiments.

Referring now to FIG. 2, a catheter assembly 29 is illustrated, according to some embodiments. In some embodiments, the catheter assembly 29 may include or correspond to the prior art catheter assembly 10. For example, one or more components of the catheter assembly 29 may include or correspond to one or more components of the prior art catheter assembly 10.

In some embodiments, the catheter assembly 29 may include a catheter adapter 36. In some embodiments, the catheter adapter 36 may include a body 38, which may include a distal end 40, a proximal end 42, and a first lumen 44 extending through the distal end 40 and the proximal end 42. In some embodiments, the catheter adapter 36 may include a side port 46 extending outwardly from the body 38. In some embodiments, the side port 46 may be disposed between the distal end 40 and the proximal end 42. In some embodiments, the side port 46 may include a second lumen 48, which may be perpendicular to the first lumen 44. In some embodiments, the second lumen 48 may extend through the side port 46 to the first lumen 44. In some embodiments, the first lumen 44 may be generally cylindrical, and the second lumen 48 may be generally cylindrical.

In some embodiments, the catheter assembly 29 may include a catheter 50, which may extend distally from the distal end 40 of the body 38 and may be secured within the catheter adapter 36. In some embodiments, the catheter assembly 29 may include a valve 52 disposed within the first lumen 44. In some embodiments, the valve 52 may seal the first lumen 44 from the second lumen 48, preventing fluid from travelling between the first lumen 44 and the second lumen 48. In some embodiments, an outer surface of the valve 52 may be cylindrical. In some embodiments, the valve 52 may be solid. In other embodiments, the valve 52 may include an opening extending through a distal end of the valve 52 and a proximal end of the valve 52. In some embodiments, the valve 52 may be constructed of silicon or another suitable material.

In some embodiments, the catheter assembly 29 may include a divider 54, which may be disposed within the second lumen 48. In some embodiments, the catheter adapter 36 and the divider 54 may be monolithically formed as a single unit, which may secure the divider 54 in response to power injection through the side port 46. In some embodiments, the divider 54 may divide the second lumen 48 into multiple openings 56. In some embodiments, the divider 54 may be constructed of plastic, metal, or another suitable material. In some embodiments, the divider 54 may be rigid.

In some embodiments, the divider 54 may be proximate the first lumen 44. In some embodiments, the divider may be disposed between an outer surface 58 of the body 38 and an inner surface 60 of the body 38 forming the first lumen 44. In some embodiments, the divider 54 may be disposed between the side port 46 and the inner surface 60 of the body 38. In some embodiments, the divider 54 may be disposed within the side port 46 or a portion of the second lumen 48 disposed within the side port 46.

In some embodiments, the divider 54 may contact the valve 52. In some embodiments, the divider 54 may be symmetrical, which may provide an evenly distributed amount of pressure on the valve 52 during power injection. In some embodiments, the divider 54 may be asymmetrical. In some embodiments, one or more of the multiple openings 56 may be identical. In some embodiments, the divider 54 may include various shapes and patterns.

In some embodiments, the divider 54 may facilitate high flow rates and maintenance of a high pressure within the catheter adapter 36 while also maintaining the integrity of the valve 52. In some embodiments, the divider 54 may increase a burst value of the valve 52 such that the valve 52 is able to withstand high pressure during power injection into the catheter adapter 36 without breaking. Thus, in some embodiments, the valve 52 may include a multi-use valve usable for multiple power injections.

In some embodiments, in response to delivering the fluid into the side port 46 at a pressure during power injection, the divider 54 may reduce or eliminate expansion of the valve 52 as the valve 52 contacts and presses upon the divider 54. In some embodiments, in response to delivering the fluid into the side port 46 at the pressure during power injection, the divider 54 may reduce or eliminate shifting of the valve 52 in a proximal direction and a distal direction.

In some embodiments, the pressure may be greater than 348 psi. In some embodiments, the pressure may be between 348 psi and 478 psi. In some embodiments, the pressure may be between 348 psi and 728 psi. In some embodiments, the pressure may be between 300 psi and 800 psi. In some embodiments, the pressure may be between 350 psi and 800 psi. In some embodiments, the pressure may be between 700 psi and 1000 psi. In some embodiments, the pressure may be between 300 psi and 400 psi, between 400 psi and 500 psi, between 500 psi and 600 psi, between 600 psi and 700 psi, between 700 psi and 800 psi, or between 800 psi and 900 psi. In some embodiments, in response to delivering the fluid into the side port 46 at the pressure, the divider 54 may inhibit expansion of the valve 52 and/or shifting of the valve 52 in the proximal direction and the distal direction. In some embodiments, the multiple openings 56 may be configured to allow fluid to flow from the side port 46 to the body 38 at a flow rate of between about 3 mL and 8 mL per second and/or at the pressure. In some embodiments, the multiple openings 56 may be configured to allow fluid to flow from the side port 46 to the body 38 at another suitable flow rate.

In some embodiments, the burst value of the valve 52 may be greater than 348 psi. In some embodiments, the burst value of the valve 52 may be between 348 psi and 478 psi. In some embodiments, the burst value of the valve 52 may be between 348 psi and 728 psi. In some embodiments, the burst value of the valve 52 may be between 300 psi and 800 psi. In some embodiments, the burst value of the valve 52 may be between 350 psi and 800 psi. In some embodiments, the burst value of the valve 52 may be between 700 psi and 1000 psi. In some embodiments, the burst value of the valve 52 may be between 300 psi and 400 psi, between 400 psi and 500 psi, between 500 psi and 600 psi, between 600 psi and 700 psi, between 700 psi and 800 psi, or between 800 psi and 900 psi. In some embodiments, the valve 52 may be stronger than body 38, which may rupture or break at a lower pressure than the valve 52.

Referring now to FIGS. 3-4, in some embodiments, the catheter adapter 36 may include another inner surface 62, which may form the second lumen 48. In some embodiments, outer edges 64 of the multiple openings 56 may form or be aligned with a shape 66 which may be an ellipse or a geometric shape, such as a circle or triangle. In some embodiments, the shape 66 may be symmetric. In some embodiments, the outer edges 64 may include arcs, which may connect two lines forming inner edges of the multiple openings 56 or ends of a single line forming an inner edge of the multiple openings 56. In some embodiments, the two lines may intersect at a corner or a rounded edge.

In some embodiments, a diameter of the shape 66, which may include a maximum diameter of the shape 66, may be less than a diameter of a portion of the other inner surface 62 that is proximate the shape 66 and closer to an outer opening 68 of the side port 46, as illustrated, for example, in FIGS. 3-4. Thus, in some embodiments, the second lumen 48 may be stepped and the divider 54 may extend from a stepped surface. In other embodiments, the diameter of the shape 66 may be equal to the diameter of the portion of the other inner surface 62 that is proximate the shape 66 and closer to an outer opening 68 of the side port 46. In these embodiments, the divider 54 may not extend from a stepped surface.

Figure 3A:
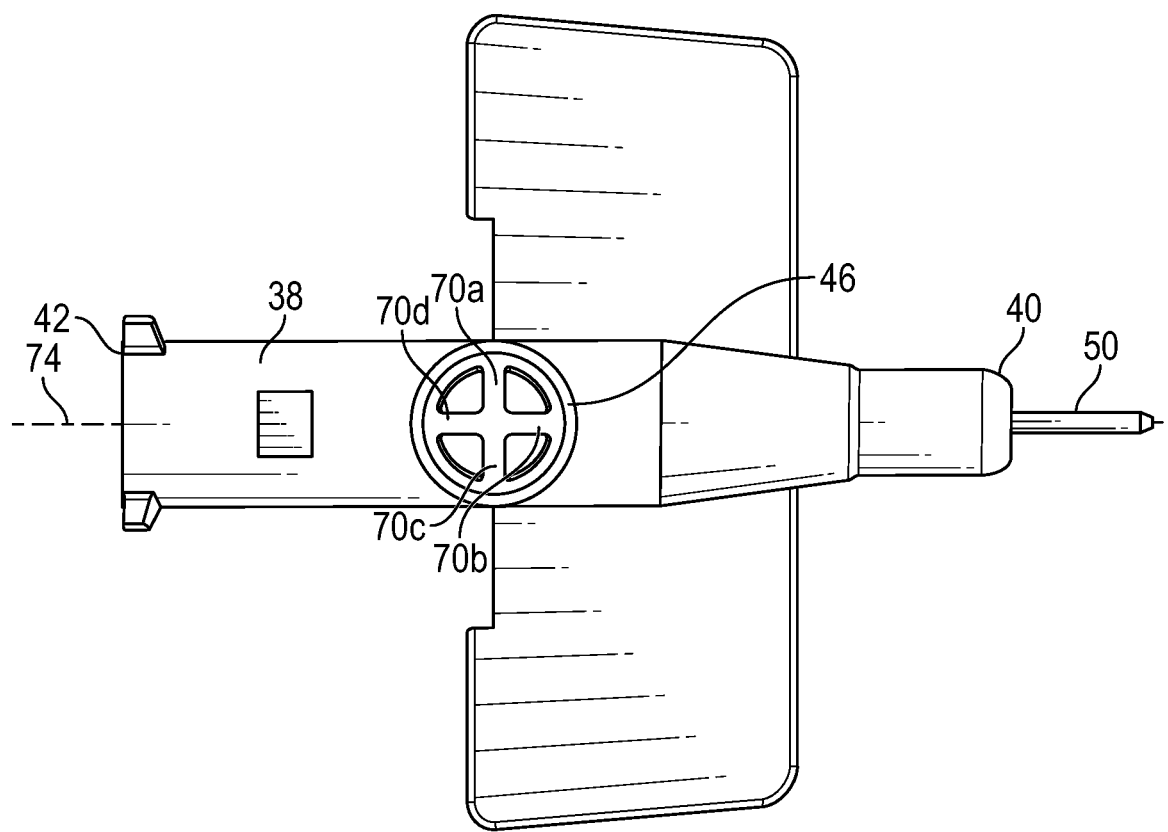
FIG. 3A is a top view of the catheter assembly of FIG. 2, illustrating an example divider and an example power injection device removed, according to some embodiments.
Figure 3B:
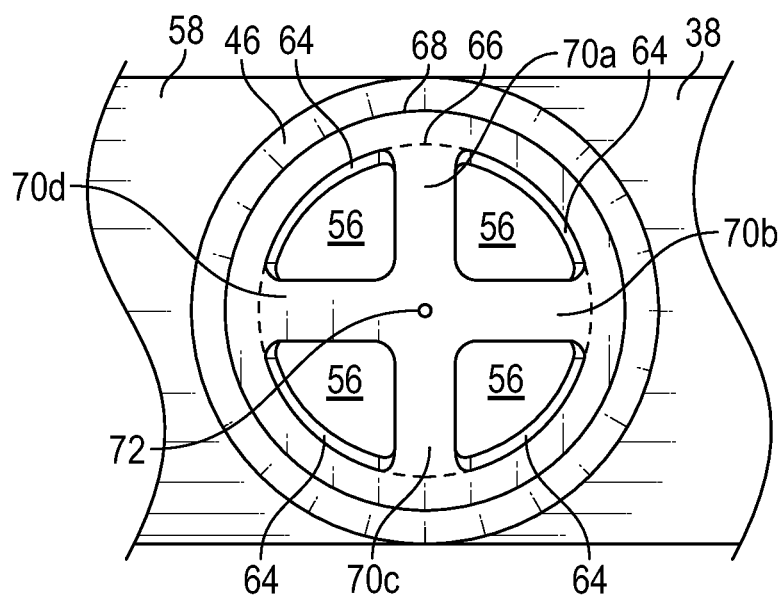
FIG. 3B is an enlarged top view of the catheter assembly of FIG. 2, illustrating the divider, according to some embodiments.
Figure 4A:
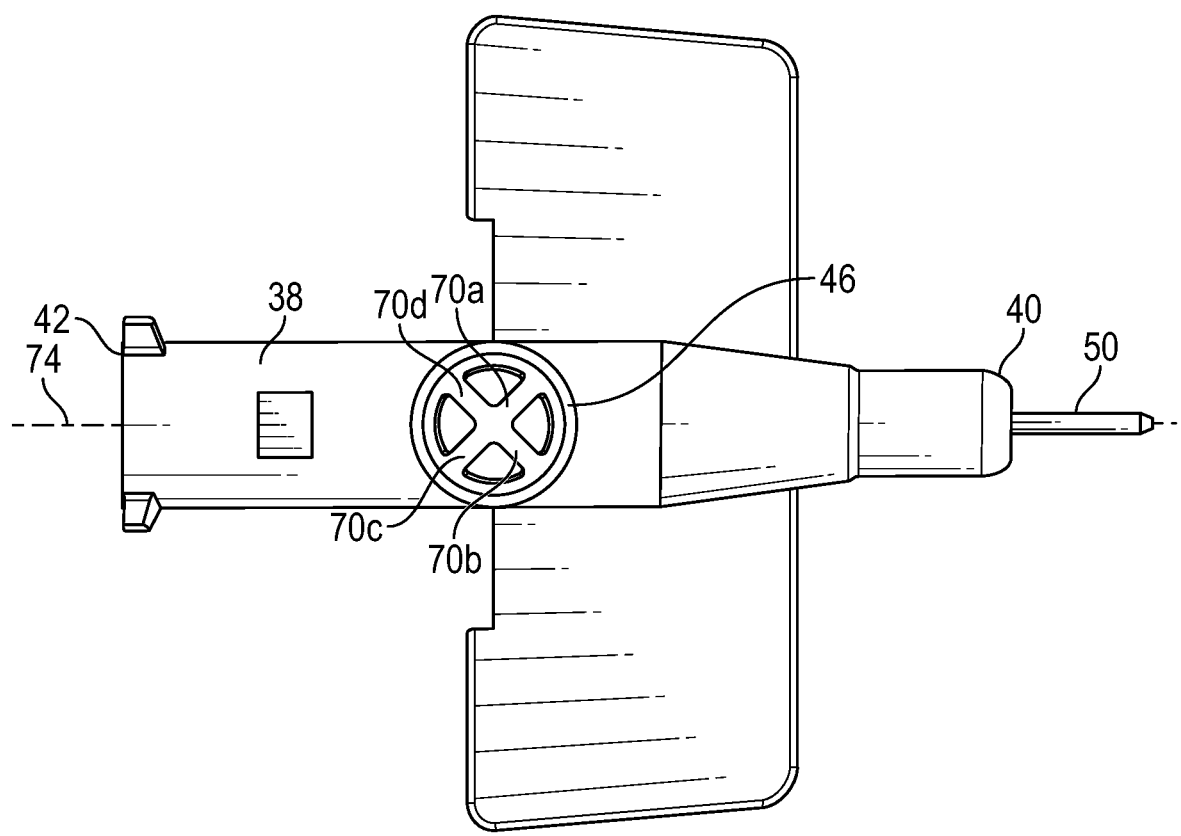
FIG. 4A is a top view of the catheter assembly of FIG. 2, illustrating another example divider and the power injection device removed, according to some embodiments.
Figure 4B:
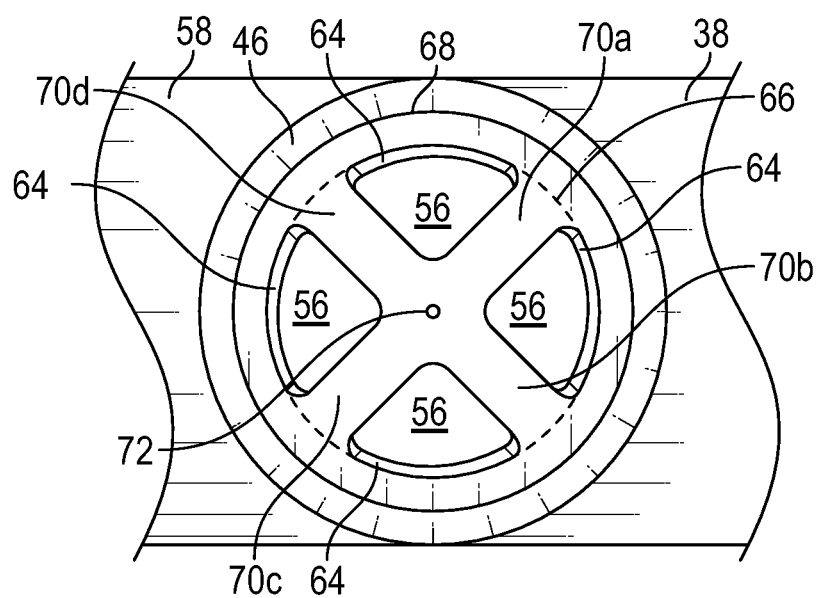
FIG. 4B is an enlarged top view of the catheter assembly of FIG. 2, illustrating the other divider of FIG. 4A, according to some embodiments.

In some embodiments, the divider 54 may include multiple arms 70, which may extend from the shape 66 to a central axis 72 (see also FIG. 2) of the second lumen 48. In some embodiments, the divider 54 may include X-shape. In these embodiments, the multiple arms 70 may include a first arm 70a, a second arm 70b, a third arm 70c, and a fourth arm 70d. In some embodiments, two of the first arm 70a, the second arm 70b, the third arm 70c, and the fourth arm 70d may be parallel to a longitudinal axis 74 (see also FIG. 2) of the catheter adapter 36, as illustrated in FIGS. 3A-3B. As illustrated in FIGS. 4A-4B, in some embodiments, the first arm 70a, the second arm 70b, the third arm 70c, and the fourth arm 70d may be offset from the longitudinal axis 74 of the catheter adapter 36, such as, for example, by about 45° or another suitable angle.

Figure 5A:
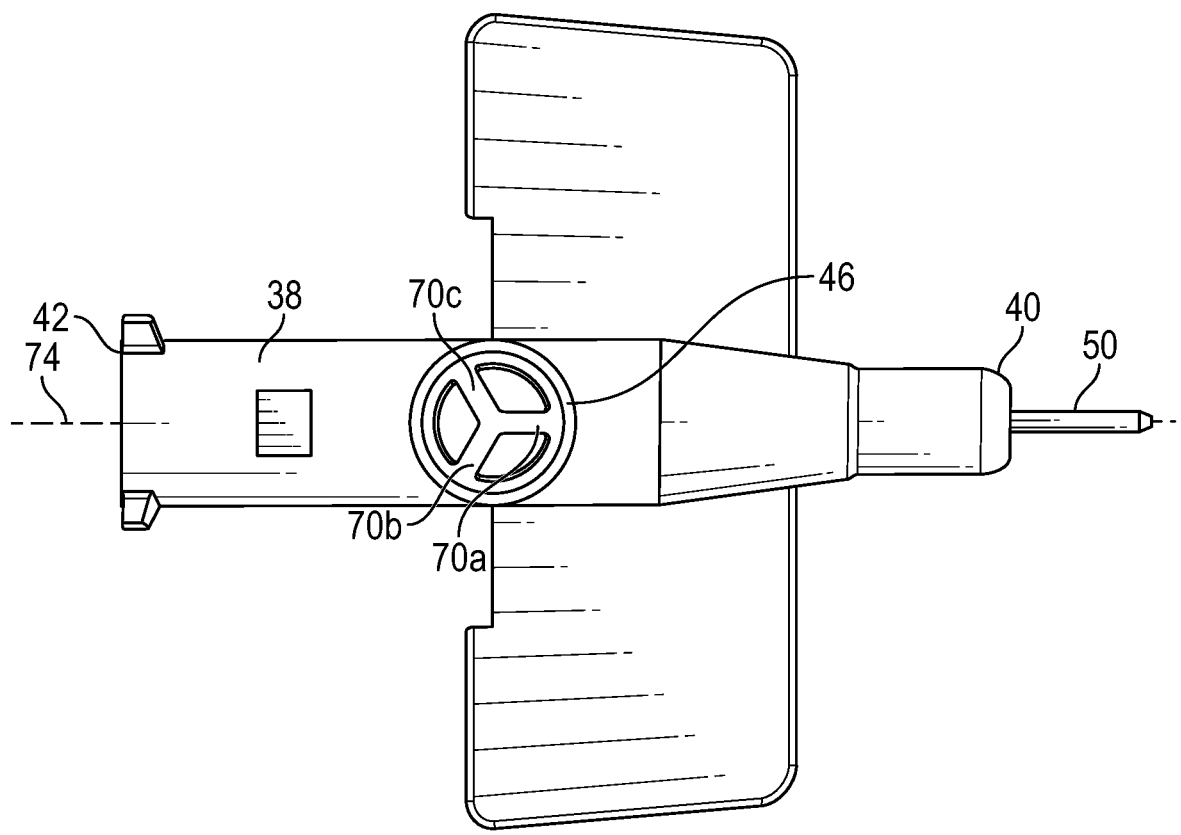
FIG. 5A is a top view of the catheter assembly of FIG. 2, illustrating another example divider and the power injection device removed, according to some embodiments.
Figure 5B:
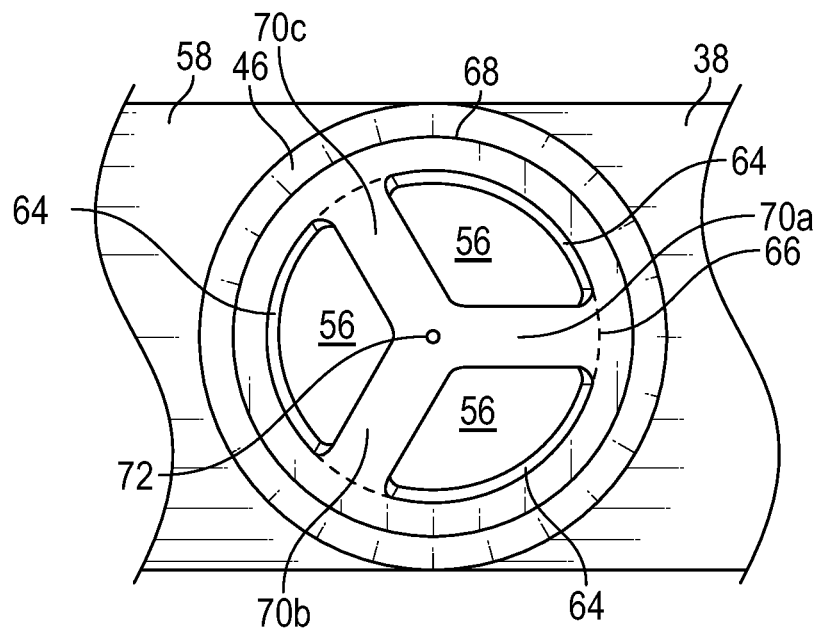
FIG. 5B is an enlarged top view of the catheter assembly of FIG. 2, illustrating the other divider of FIG. 5A, according to some embodiments.
Figure 6A:
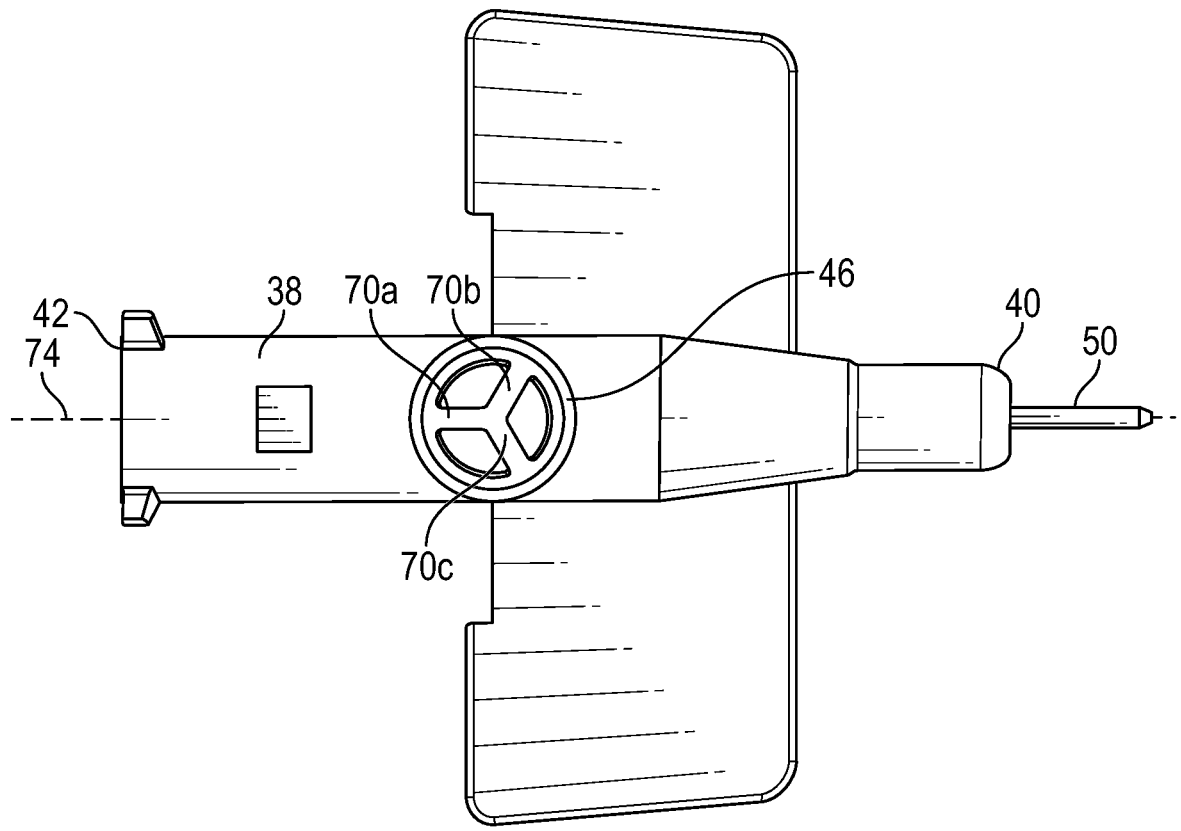
FIG. 6A is a top view of the catheter assembly of FIG. 2, illustrating another example divider and the power injection device removed, according to some embodiments.
Figure 6B:
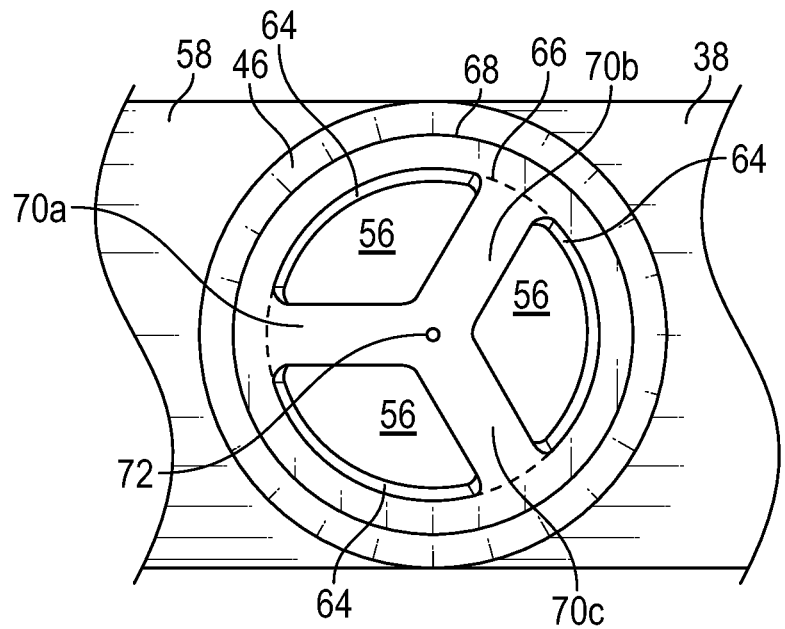
FIG. 6B is an enlarged top view of the catheter assembly of FIG. 2, illustrating the other divider of FIG. 6A, according to some embodiments.

Referring now to FIGS. 5-6, in some embodiments, the divider 54 may include a Y-shape. In these embodiments, the multiple arms 70 may include the first arm 70a, the second arm 70b, and the third arm 70c. In some embodiments, one of the first arm 70a, the second arm 70b, and the third arm 70c may be parallel to the longitudinal axis 74 of the catheter adapter 36 and may point distally, as illustrated in FIGS. 5A-5B. As illustrated in FIGS. 6A-6B, in some embodiments, one of the first arm 70a, the second arm 70b, and the third arm 70c may be parallel to the longitudinal axis 74 of the catheter adapter 36 and may point proximally. In some embodiments, none of the first arm 70a, the second arm 70b, or the third arm 70c may be aligned with the longitudinal axis 74 of the catheter adapter 36.

Figure 7A:
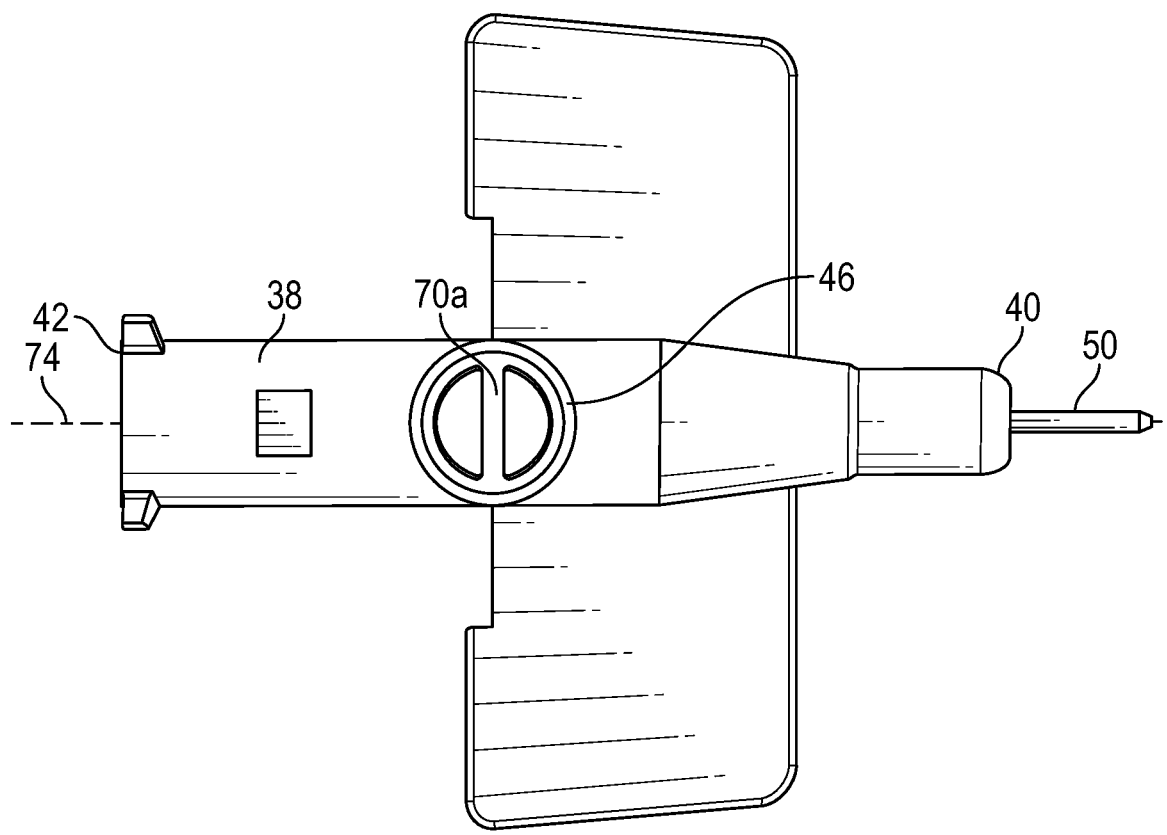
FIG. 7A is a top view of the catheter assembly of FIG. 2, illustrating another example divider and the power injection device removed, according to some embodiments.
Figure 7B:
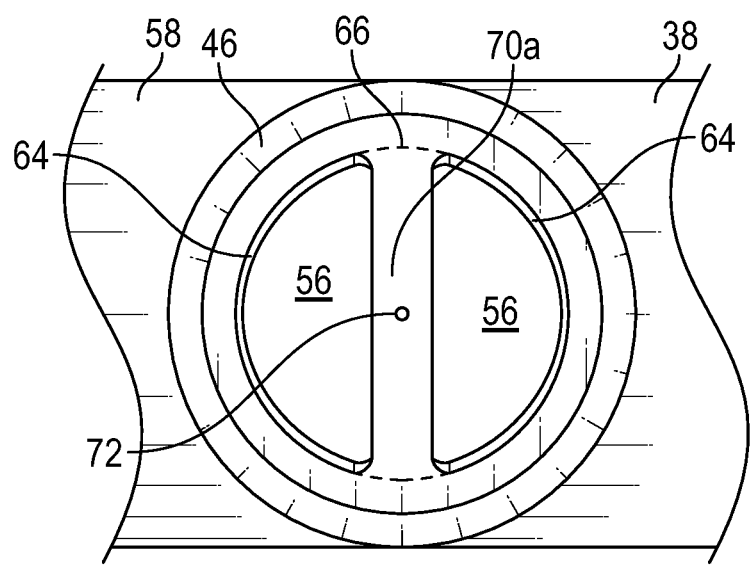
FIG. 7B is an enlarged top view of the catheter assembly of FIG. 2, illustrating the other divider of FIG. 7A and the power injection device removed, according to some embodiments.
Figure 8A:
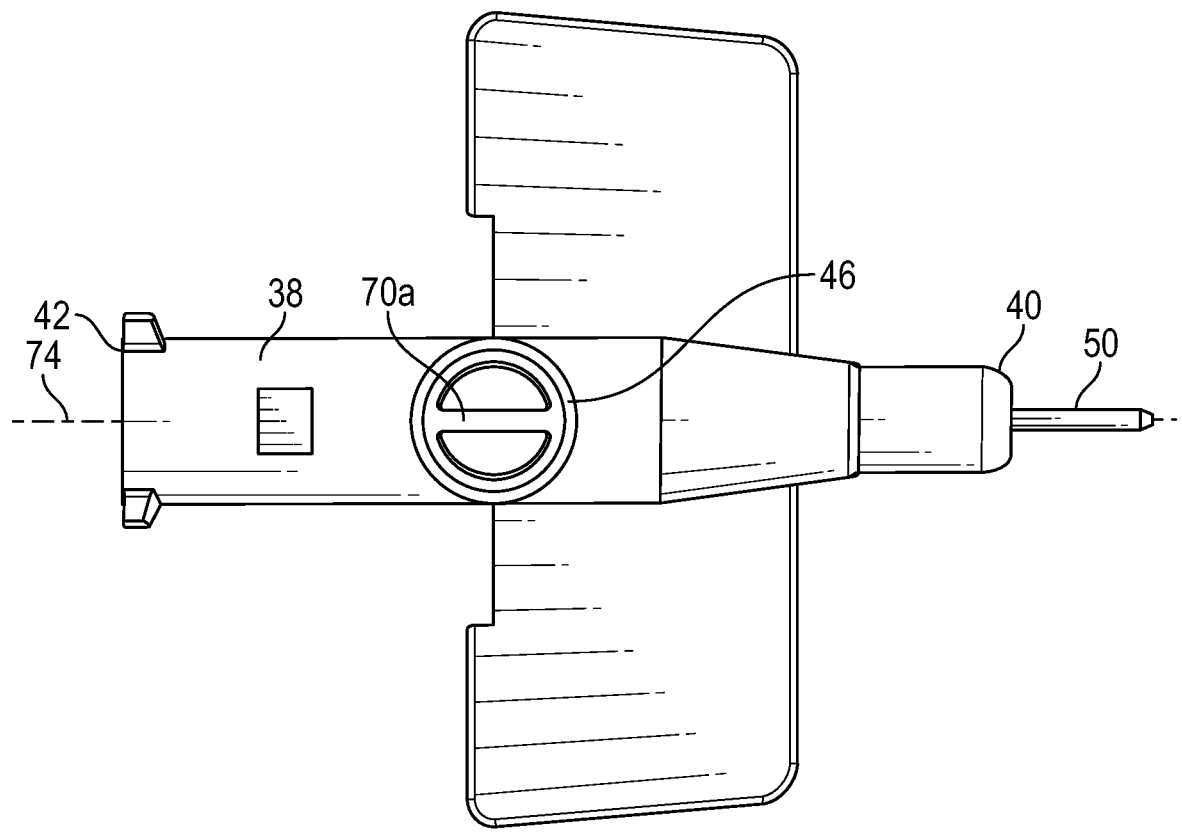
FIG. 8A is a top view of the catheter assembly of FIG. 2, illustrating another example divider and the power injection device removed, according to some embodiments.
Figure 8B:
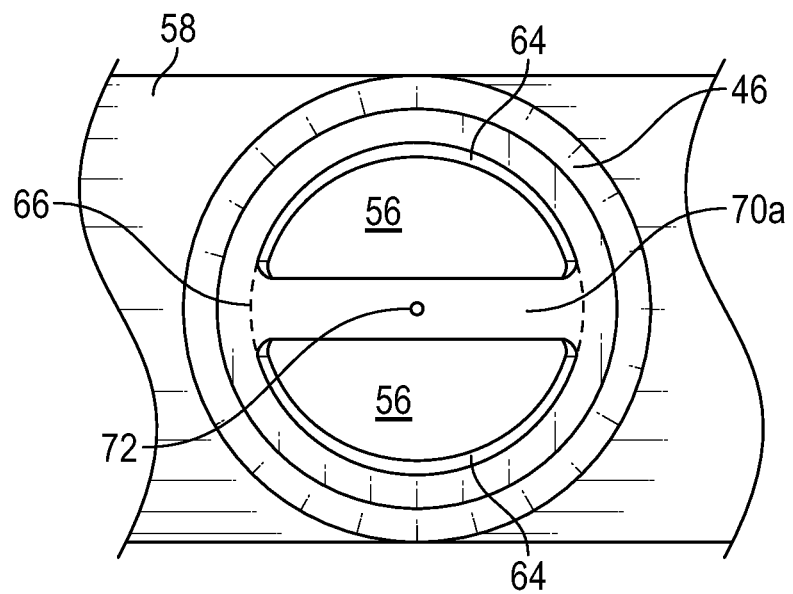
FIG. 8B is an enlarged top view of the catheter assembly of FIG. 2, illustrating the other divider of FIG. 8A and the power injection device removed, according to some embodiments.

Referring now to FIGS. 7-8, in some embodiments, the divider 54 may be linear and may extend from one side of the shape 66 to another side of the shape 66. In some embodiments, the divider 54 that is linear and/or oriented perpendicular to the longitudinal axis 74 of the catheter adapter 36 may reduce leakage of fluid between the outer surface of the valve 52 and the inner surface 60 of the body 38 that might otherwise shift the valve 52 in the proximal direction or the distal direction during power injection. In some embodiments, the divider 54 may be perpendicular to the longitudinal axis 74 of the catheter adapter 36, as illustrated in FIGS. 7A-7B. In some embodiments, the divider 54 may be parallel to the longitudinal axis 74 of the catheter adapter 36, as illustrated in FIGS. 8A-8B.

In some embodiments, a method of delivering fluid into the catheter adapter 36 may include coupling the power injection device 26 to the side port 14 of the catheter adapter 12. In some embodiments, the method may include delivering fluid, via the power injection device 26, into the side port 14 at the pressure. In some embodiments, an integrity of the valve 52 may be maintained in response to delivering the fluid into the side port 14 at the pressure. In some embodiments, the pressure may not exceed the burst value of the valve 52.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising:
a catheter adapter, comprising:
a body, comprising a distal end, a proximal end, and a first lumen extending through the distal end and the proximal end;
a side port extending outwardly from the body and disposed between the distal end and the proximal end, wherein the side port comprises a second lumen perpendicular to the first lumen;
a catheter extending distally from the distal end of the body;
a valve disposed within the first lumen and sealing the first lumen from the second lumen, wherein an outer surface of the valve is cylindrical; and
a divider disposed with the second lumen, wherein the divider divides the second lumen into a plurality of openings.

2. The catheter assembly of claim 1, wherein the divider is proximate the first lumen.

3. The catheter assembly of claim 1, wherein the divider contacts the valve.

4. The catheter assembly of claim 1, wherein the divider is symmetrical.

5. The catheter assembly of claim 4, wherein each of the plurality of openings is identical.

6. The catheter assembly of claim 1, wherein outer edges of the plurality of openings form a symmetrical shape, wherein the divider is linear and extends from one side of the symmetrical shape to another side of the symmetrical shape.

7. The catheter assembly of claim 6, wherein the divider is perpendicular to a longitudinal axis of the catheter adapter.

8. The catheter assembly of claim 6, wherein the divider is parallel to a longitudinal axis of the catheter adapter.

9. The catheter assembly of claim 1, wherein outer edges of the plurality of openings form a symmetrical shape, wherein the divider comprises a plurality of arms that extend from the symmetrical shape to a central axis of the second lumen.

10. The catheter assembly of claim 9, wherein the divider comprises a X-shape.

11. The catheter assembly of claim 10, wherein the plurality of arms comprises a first arm, a second arm, a third arm, and a fourth arm, wherein two of the first arm, the second arm, the third arm, and the fourth arm are parallel to a longitudinal axis of the catheter adapter.

12. The catheter assembly of claim 10, wherein the X-shape comprises a first arm, a second arm, a third arm, and a fourth arm, wherein the first arm, the second arm, the third arm, and the fourth arm are offset from a longitudinal axis of the catheter adapter.

13. The catheter assembly of claim 10, wherein the divider comprises a Y-shape.

14. The catheter assembly of claim 13, wherein the plurality of arms comprises a first arm, a second arm, and a third arm, wherein one of the first arm, the second arm, and the third arm is parallel to a longitudinal axis of the catheter adapter and points distally.

15. The catheter assembly of claim 13, wherein the plurality of arms comprises a first arm, a second arm, and a third arm, wherein one of the first arm, the second arm, and the third arm is parallel to a longitudinal axis of the catheter adapter and points proximally.

16. The catheter assembly of claim 1, wherein the catheter adapter and the divider are monolithically formed as a single unit.

17. A method of delivering fluid into a catheter adapter, comprising:
  coupling a power injection device to a side port of a catheter adapter of a catheter assembly, wherein the catheter assembly comprises:
    a catheter adapter, comprising:
      a body, comprising a distal end, a proximal end, and a first lumen extending through the distal end and the proximal end;
      a side port extending outwardly from the body and disposed between the distal end and the proximal end, wherein the side port comprises a second lumen perpendicular to the first lumen;
    a catheter extending distally from the distal end of the body;
    a valve disposed within the first lumen and sealing the first lumen from the second lumen, wherein an outer surface of the valve is cylindrical; and
    a divider disposed with the second lumen, wherein the divider divides the second lumen into a plurality of openings;
  delivering fluid, via the power injection device, into the side port at a pressure,
  wherein the pressure is greater than 348 psi, wherein an integrity of the valve is maintained in response to delivering the fluid into the side port at the pressure.

18. The method of claim 17, wherein the pressure is between 348 psi and 728 psi.

19. The method of claim 17, wherein the pressure is between 348 psi and 478 psi.

20. The method of claim 17, wherein in response to delivering the fluid into the side port at the pressure the divider inhibits expansion of the valve and shifting of the valve in a proximal-distal direction.

* * * * *